United States Patent [19]

Köhler et al.

[11] Patent Number: 5,047,556

[45] Date of Patent: Sep. 10, 1991

[54] PHOTOINITIATORS HAVING A COMBINED STRUCTURE

[75] Inventors: Manfred Köhler, Dormstadt; Jörg Ohngemach, Reinheim, both of Fed. Rep. of Germany

[73] Assignee: Merck Patent Gesellschaft Mit Beschränkter Haftung, Darmstadt, Fed. Rep. of Germany

[21] Appl. No.: 390,940

[22] Filed: Aug. 8, 1989

[30] Foreign Application Priority Data

Aug. 9, 1988 [DE] Fed. Rep. of Germany ....... 3826947

[51] Int. Cl.$^5$ .......................................... C07D 335/10
[52] U.S. Cl. ...................................................... 549/27
[58] Field of Search ............................................ 549/27

[56] References Cited

FOREIGN PATENT DOCUMENTS 0003002 7/1979 European Pat. Off. .
2722264 11/1978 Fed. Rep. of Germany .
2482102 5/1981 France .

OTHER PUBLICATIONS

Chemical Abstracts Service 96:143533 Abstract of French patent 2,482,102.

*Primary Examiner*—Catherine S. Kilby Scalzo

[57] ABSTRACT

The invention relates to photoinitiators having a combined structure

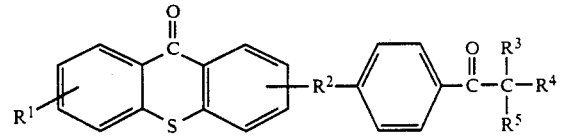

and their use as photoinitiators in the photopolymerization of ethylenically unsaturated compounds or binder systems containing them.

6 Claims, No Drawings

PHOTOINITIATORS HAVING A COMBINED STRUCTURE

The invention relates to photoinitiators having a molecular structure which is a combination of different photoinitiator basic structural types. These photoinitiators having a combined structure serve as photoinitiators for the photopolymerization of ethylenically unsaturated compounds or binder systems containing them. In this connection, they exhibit, in many cases, a number of unexpected advantages compared with the photoinitiator individual structures or the mixtures thereof on which they are based.

BACKGROUND OF THE INVENTION

Photochemically produced polymerization reactions have become of great importance in industry, in particular for rapid curing of thin films, such as, for example, in the curing of paint coatings and plastic coatings on paper, wood, metal, and plastic or in the drying of printing inks. This curing by irradiation in the presence of photoinitiators is distinguished, compared with conventional methods for the drying or curing of coatings, by saving of materials and energy, low thermal stress of the substrate, and in particular a high curing rate. Moreover, the preparation of polymer materials per se by polymerization of the corresponding unsaturated monomeric starting materials is often carried out photochemically and by means of photoinitiators in such conventional processes as solution and emulsion polymerization.

Since in the reactions mentioned, none of the reactants is usually capable of absorbing a sufficient amount of the photochemically active radiation, it is necessary to add photoinitiators. The photoinitiators are capable of either absorbing the incoming high energy radiation, in most cases UV light, and forming active starter radicals during this process, which in turn initiate the photopolymerization, or transferring the energy absorbed to one of the polymerizable reactants for the purpose of radical formation. Usually, the initiators do not take part in the polymerization reaction itself.

Photoinitiators which are suitable for this purpose are predominantly compounds of the type of aromatic ketones, such as benzophenone, benzil, or thioxanthones, and of the type of α-substituted alkylphenones, such as benzoin ethers, benzil monoketals, dialkoxyacetophenones, or hydroxyalkylphenones, and derivatives derived from these structural types.

The increasing diversification and specialization of processes and products in the area of coating techniques using polymer materials and the more and more frequent requirement of providing tailor-made solutions for these problems have the result that increasingly higher and more specific demands are also made on the photoinitiators. Therefore, in many cases, photoinitiators of the conventional type do not fulfill, or at least not to an optimum degree, the demand made on them today.

The major problems involved are the achievement of maximum photoinitiator activity, in particular also that in pigmented systems, compatibility with a wide range of binder systems, their reactive components and other modifying additives, the storage stability in the dark of the systems containing the initiator and the possible deterioration in the quality of the cured final product, such as yellowing, as a result of unconverted initiator residues and initiator degradation products.

Photoinitiators of the type of aromatic ketones, such as, in particular, benzophenone and thioxanthone and derivatives thereof, belong, as is known, to the group of "intermolecular H abstractors". The photoinitiators of the type of α-substituted alkylphenones, belong to the group of "intramolecular α-cleavers". Intramolecular α-cleavers disintegrate, after excitation and transition to the excited triplet state, into two active starter radicals.

Intermolecular H abstractors require coinitiators for effective activity; in most cases, amines are used for this purpose, from which they abstract in the excited triplet state a hydrogen atom and thus form the active starter radical.

Of the large number of known photoinitiators, the hydroxyalkylphenone photoinitiators, such as are described in German Patent Specification 2,722,264 and European Patent Specification 3002, have proven to be particularly advantageous, in particular because of their high reactivity, but also because of the excellent storage stability in the dark of the irradiation-curable systems to which they have been added and because the films cured therewith have little tendency to yellow. However, these compounds absorb predominantly in the medium to lower UV wavelength region and are, therefore, less favorable for pigmented systems. Especially in systems pigmented by means of titanium dioxide, a large proportion of the active wavelength is absorbed by the pigment, so that higher initiator concentrations and/or additional spectral sensitizers must be used.

Thioxanthone photoinitiators absorb in the higher wavelength region of the UV, in particular also in an "absorption window" of titanium dioxide, so that they are predestined especially in this regard for use in systems pigmented with titanium dioxide. However, thioxanthones have the disadvantage that they are predominantly sparingly soluble and only sufficiently active in combination with coinitiators. Moreover, systems containing thioxanthone/amine mixtures have a very strong tendency to yellow, which is very undesirable, especially in white-pigmented systems.

Mixtures of hydroxyalkylphenones and thioxanthones have proven to be more favorable for pigmented systems. The higher reactivity of this type of mixtures compared with the pure hydroxyalkylphenones is probably due to a certain spectral sensitization in the longer wavelength region, which is caused by the thioxanthone.

However, in many cases, the known photoinitiators and photoinitiator combinations do not sufficiently fulfill the increased demands made on them today.

SUMMARY OF THE INVENTION

It was, therefore, an object of this invention to find and provide more efficient photoinitiators, which are also suitable in particular for pigmented systems.

Upon further study of the specification and appended claims, further objects and advantages of this invention will become apparent to those skilled in the art.

It has now been found that above objects can be met in every respect by compounds of the formula I

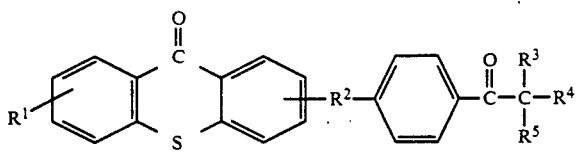

(I)

in which

R¹ is hydrogen, halogen, $C_{1-6}$-alkyl, $C_{1-6}$-alkoxy, $C_{1-6}$-alkylthio, $NO_2$ $R_2$ is $COO\text{-}(CH_2)_m\text{-}X$ or $X\text{-}(CH_2)_m\text{-}Y\text{-}CO\text{-}(CH_2)_n\text{-}X$, where X is O, S and Y is O, NH, m is a number from 2 to 10 and n is a number from 1 to 10

$R^3$, $R^4$, independently of one another, are each H, $C_{1-12}$-alkyl, $C_{2-12}$-alkenyl or together $C_{2-6}$-alkylene $R^5$ is $OR^6$, $N(R^6)_2$,

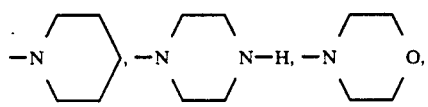

$SO_2R^7$, $OSO_2R^7$ $R^6$ is H, $C_{1-6}$-alkyl or $C_{1-6}$-alkanoyl $R^7$ is $C_{1-6}$-alkyl or phenyl or benzyl which is unsubstituted or in each case substituted by halogen, $C_{1-6}$-alkyl or $C_{1-6}$-alkoxy.

The invention accordingly relates to compounds of the formula I.

The invention further relates to the use of the compounds of the formula I as photoinitiators for the photopolymerization of ethylenically unsaturated compounds or of binder systems containing them.

Moreover, the invention relates to photopolymerization binder systems containing at least one ethylenically unsaturated photopolymerizable compound and, if necessary, further known and customary additives, which in addition contain at least one compound of the formula I as photoinitiator.

The invention finally provides a process for the preparation of an irradiation-cured coating on a substrate, in which this substrate is coated by means of a photopolymerizable binder system containing at least one compound of the formula I as photoinitiator and the curing is carried out by irradiation with UV light of a wavelength between 250 and 450 nm.

The compounds of the formula I are new. They are photoinitiators having a molecular structure which is a combination of two different photoinitiator basic structural types, namely of the thioxanthone type on the one hand and of the type of α-substituted alkylphenones on the other.

In formula I, a thioxanthone radical, which may carry a substituent R¹, which can be halogen, such as, in particular, chlorine, $C_{1-6}$-alkyl, $C_{1-6}$-alkoxy, $C_{1-6}$-alkylthio or $NO_2$, is linked to the aromatic ring of an α-substituted alkylphenone radical via a bridge grouping $R^2$. The linkage of the bridge grouping $R^2$ to the thioxanthone structural unit can take place in the 1-, 2-, 3- or 4-position, preferably in the 1-, 2- or 3-position, in particular in the 1- or 3-position. In the alkylphenone radical, the substituents $R^3$ and $R^4$ on the carbon atom which is in the α-position relative to the carbonyl group can be hydrogen, $C_{1-12}$-alkyl, $C_{2-12}$-alkenyl or together $C_{2-6}$-alkylene. Preferably, $R^3$ and $R^4$ are each methyl. The substituent $R^5$ can be a hydroxyl, a $C_{1-6}$-alkoxy, a $C_{1-6}$alkanoyl group, a dialkylamino or dialkanoylamino group in which the alkyl and alkanoyl groups can each have up to 6 carbon atoms, an N-piperidino, an N-piperazino or an N-morpholino group. Preferred photoinitiator structural units are those in which R° is a hydroxyl or N-morpholino group. Photoinitiator structural units of the hydroxyalkylphenone type are particularly preferred. The bridge groupings $R^2$ can be alkylene groups and grouping consisting of alkylene groups linked by means of ester or amide groups, which in turn are linked to the photoinitiator structural units via carboxyl, oxygen or sulfur atoms. Preferred bridge groupings are carbonyloxyethyleneoxy, carbonyloxyethylenethio, oxymethylenecarbonyloxyethylenethio and oxymethylenecarbonylamidoethylenethio groups.

Typical examples of compounds of the formula I are 1-(1-thioxanthonylcarbonyloxy)-2-[4-(2-hydroxy-2-methyl)-propanoylphenoxy]ethane

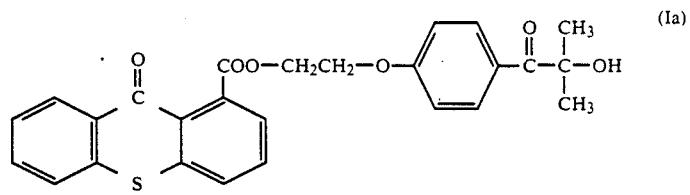

(Ia)

1-(1-thioxanthonylcarbonyloxy)-2-[4-(2-hydroxy-2-methyl)-propanoylphenylthio]ethane

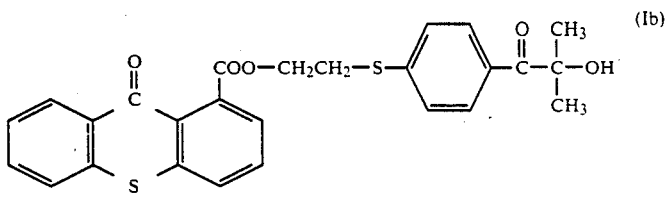

(Ib)

1-(1-thioxanthonylcarbonyloxy)-2-[4-(2-N-morpholino-2-methyl)propanoylphenoxy]ethane

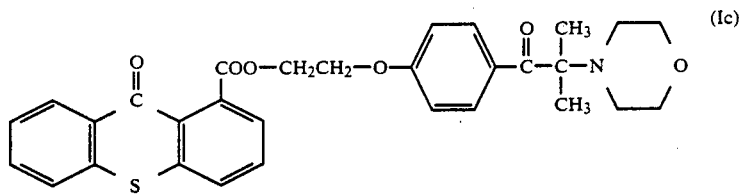

1-(1-thioxanthonylcarbonyloxy)-2-[4-(2-N-morpholino-2-methyl)propanoylphenylthio]ethane

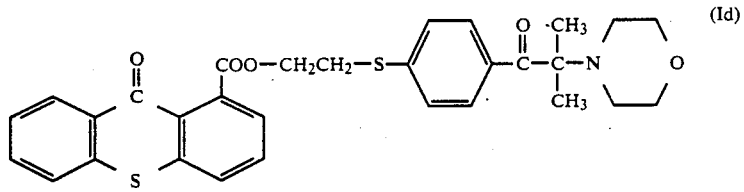

1-(3-thioxanthonylthio)-2-[4-(2-hydroxy-2-methyl)-propanoylphenoxymethylenecarbonyloxy]ethane

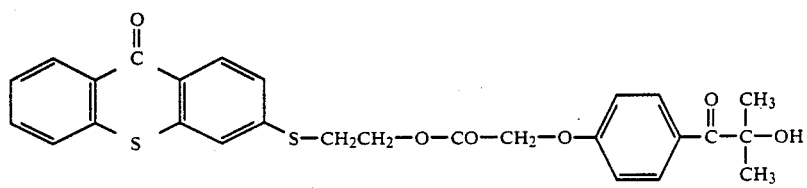

1-(3-thioxanthonylthio)-2-[4-(2-hydroxy-2-methyl)-propanoylphenoxymethylenecarbonylamido]ethane

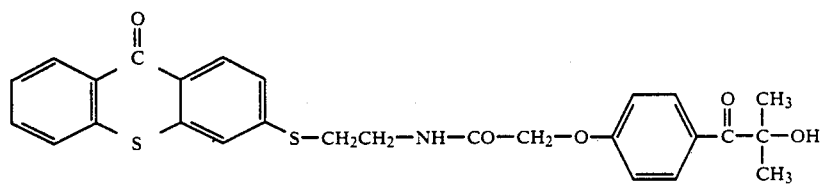

The compounds of the formula I are prepared by means of customary reactions, such as, in particular, esterification reactions, from appropriately functionalized derivatives of the underlying thioxanthone and alkylphenone units.

The conditions of these reactions are as usual and can be found in the standard works of preparative organic chemistry, e.g. HOUBEN-WEYL, Methoden der organischen Chemie (Methods of Organic Chemistry), GeorgThieme Verlag, Stuttgart or ORGANIC SYNTHESIS, J. Wiley, New York, London, Sydney.

The preferred functionalized derivatives of the photoinitiator basic structures are those which already contain in the molecule the eventual bridge grouping $R^2$ or the corresponding precursors or partial structures thereof. The corresponding compounds are thioxanthone or alkylphenone derivatives which contain, for instance, hydroxyethoxy, hydroxyethylthio, hydroxycarbonyl or hydroxycarbonylmethyleneoxy groups. Functionalized photoinitiator derivatives of this type have been described in detail in German Patent Applications P 3,707,891 and P 3,738,567 (U.S. Pat. Appln. Ser. No. 167,060). Thus, for example, the compounds Ia to Id can be obtained by reaction of thioxanthone-1-carboxylic acid with hydroxyethoxy or hydroxyethylthio derivatives of the corresponding alkylphenones or their methosulfates. The compounds Ie and If are obtained by reaction of 3-hydroxyethoxy- or 3-hydroxyethylthiothioxanthone or their methosulfates with hydroxycarbonylethyleneoxy-functionalized alkylphenones.

The photoinitiators according to the invention having a combined structure can be very advantageously used as photoinitiators for the photopolymerization of ethylenically unsaturated compounds or of binder systems containing them. Predominantly, they serve analogously to conventional photoinitiators as UV curing agents for paint or polymer coatings and printing inks based on UV curable binder or hybrid binder systems, which may also be present in the form of aqueous dispersions. They are applied in the usual manner, such that the amounts added to the binder systems are, as a rule, 0.1 to 20 % by weight, preferably 1 to 10 % by weight. This addition is usually carried out by stirring them directly into the binder system, if necessary, with the additional use of a minor amount of a compatible solvent. In this respect the compounds of the formula I display very favorable properties with respect to their solubility and homogeneous miscibility with virtually all customary irradiation-curable systems and also with respect to the storage stability in the dark of the systems to which they have been added.

A particular advantage is the surprisingly high reactivity of the photoinitiators according to the invention having a combined structure compared with the corresponding underlying photoinitiator types and their mixtures. This is especially also true for pigmented systems. Thus, if the compounds of the formula I are used in equivalent amounts and under comparable curing conditions, higher layer hardnesses can be obtained compared with mixtures of thioxanthone and hydroxyalkylphenone photoinitiators. One possible explanation is that a direct sensitizing and/or coinitiating interaction between the different initiator groups may occur as a result of the sterically close fixation in the molecule.

A photopolymerizable binder system is usually understood to mean a mixture containing at least one ethylenically unsaturated compound photopolymerizable by free radicals and, if necessary, further conventional additives. Suitable components polymerizable by free radicals are virtually all materials which have olefinically unsaturated double bonds. They can be in particular monomers, oligomers and polymers each having at least one or, advantageously, several unsaturated functions of the acrylate or vinyl type. The corresponding materials are known to one skilled in the art in large numbers. Examples of these types of compounds are acrylic compounds, in particular acrylates of aliphatic and aromatic monoor polyhydroxy compounds, such as, for example, (meth)acrylic acid, including their salts and amides, (meth)acrylonitrile, alkyl (meth)acrylates, hydroxyethyl (meth)acrylate, vinyl (meth)acrylate, ethylene glycol di(meth)acrylate, 1,6-hexanediol di(meth)acrylate, trimethylolpropane di(meth)acrylate, pentaerythritol tri(meth)acrylate, furthermore vinyl compounds such as, for example, vinyl chloride, vinylidene chloride, styrene, divinylbenzene, N-vinylpyrrolidone and N-vinylcarbazole. Examples of higher-molecular-weight and polymeric binder components are acrylated polyester, acrylate, epoxy, urethane, polyamide and silicone resins. Predominantly, irradiation-curable binder systems are mixtures of several of the lower-molecular-weight and higher-molecular-weight unsaturated components.

Hybrid binder systems additionally contain, apart from these, components which can be crosslinked thermally, for example by polycondensation or polyaddition, but not by free radicals. Examples of these are acid-curable melamine resins and polyurethane- or polyester-forming reactive resins.

The irradiation-curable binder systems can also be present in the form of aqueous dispersions, the water content of which is usually removed after the completion of the coating by heating for a short time.

The binder systems curable by means of the compounds of the formula I as photoinitiators can be varied in their qualitative and quantitative compositions over a wide range and can also contain in particular further components and additives. Advantageously, the content of reactive components should not be less than 10 % by weight. Further components and additives in the amounts which are appropriate and customary for the particular purpose can be inorganic and organic pigments, dyes, fillers, flow-improving agents, surface-active agents, light stabilizers and antioxidants, thixotropic agents, delustering agents, plasticizers, solvents, dispersants, further binders and resins, other photoinitiators, spectral sensitizers and coinitiators of known types, further thermal reactive or photoreactive radical initiators and cation- or acid-forming catalysts.

The binder systems mentioned can be cured according to the invention by means of the compounds of the formula I by exposing them to radiation energy, in particular from the UV wavelength region. In certain cases, especially in the case of hybrid binder systems, it is advantageous to promote the curing process by simultaneous or subsequent application of thermal energy.

The photopolymerization is carried out by methods known per se by irradiation with light or UV radiation of the wavelength region of 250-450nm, preferably 300-400 nm. The radiation sources used can be the customary mercury vapor high-pressure, mercury vapor medium-pressure or mercury vapor low-pressure lamps and xenon and tungsten lamps.

The photopolymerization using the photoinitiator according to the invention having a combined structure can be carried out either batchwise or continuously. The irradiation time depends on the type of procedure, the type and amount of the polymerizable materials used, the type and concentration of the photoinitiators used and the intensity of the light sources. In the irradiation curing of coatings, it is usually in the range from a few seconds to minutes.

The compounds of the formula I according to the invention are preferably used as photoinitiators in the UV-curing of thin films such as, for example, paint coatings on all customary materials and substrates. These can predominantly be paper, wood, textile substrates, plastic and metal. Another important area of application is the drying or curing of printing inks and screen-printing materials, the latter of which are preferably used in the surface coating or surface design of, for example, cans, tubes and metal screw-caps.

Their easy availability and their excellent properties in industrial application, in particular their high reactivity in pigmented systems, render the photoinitiators according to the invention having a combined structure particularly valuable for the practical application.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire texts of all applications, patents, and publications, cited above and below, and of corresponding West German Application No. P 38 26 947.3, filed Aug. 9, 1988, is hereby incorporated by reference.

Example 1

1-(1-Thioxanthonylcarbonyloxy)-2-[4-(2-hydroxy-2-methyl)propanoylphenoxy]ethane (Ia)

2.6 g (0.01 mol) of thioxanthone-1-carboxylic acid were added with stirring at room temperature to 0.3 g of sodium and 50 ml of methanol, the mixture was stirred at the reflux temperature for 1 hour, and the solvent was then distilled off. 3.0 g (0.01 mol) of 4-(2methylsulphonyloxyethoxy)phenyl (2-hydroxy-2-propyl) ketone were added to the residue, and the mixture was stirred at 80° C. for 3 hours. After cooling, water was added, and the mixture was extracted with ethyl acetate. Removal of the solvent and recrystallization of the residue from methyl ethyl ketone gave 1.4 g of compound Ia in the form of a yellowish crystalline powder of melting point 160° C.

The following compounds were obtained analogously 1-(1-thioxanthonylcarbonyloxy)-2-[4-(2-hydroxy-2-
   methyl)propanoylphenylthio]ethane (Ib)
(1-thioxanthonylcarbonyloxy)-2-[4-(2-N-morpholino-
   2methyl)propanoylphenoxy]ethane (Ic)
1-(1-thioxanthonylcarbonyloxy)-2-[4-(2-N-morpholino-
   2methyl)propanoylphenylthio]ethane (Id) m.p. 134°
   C.

Example 2

1-(3-Thioxanthonylthio)-2-[4-(2-hydroxy-2-methyl)-
propanoylphenoxymethylenecarbonyloxy]ethane (Ie)

50 ml of DMSO and 2.4 g (0.01 mol) of 4-(hydroxycarbonylmethoxy)phenyl (2-hydroxy-2-propyl) ketone were added to 1.2 g of potassium t-butoxide, and the mixture was stirred at room temperature for 1 hour. It was then heated to 70° C., 3.7 g (0.01 mol) of 3-(2-methylsulfonyloxyethylthio)thioxanthone were added, and the mixture was stirred at this temperature for 4 hours. Work-up as in Example 1 and recrystallization from toluene gave 2.1 g of compound Ie of melting point 114° C.

The compound 1-(3-thioxanthonylthio)-2-[4-(2-hydroxy-2-methyl)propanoylphenoxymethylenecarbonylamido]-ethane (If) was obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the inventions to adapt it to various usages and conditions.

What is claimed is:
1. A compound of the formula

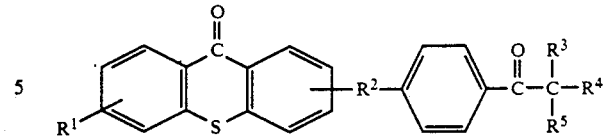

in which
R$^1$ is hydrogen, halogen, C$_{1-6}$-alkoxy, C$_{1-6}$alkylthio, or NO$_2$;
R$_2$ is COO-(CH$_2$)$_m$-X or X-(CH$_2$)$_m$-Y-CO-(CH$_2$)$_n$-X, where X is O or S, Y is O or NH, m is a number from 2 to 10 and n is a number from 1 to 10;
R$^3$, R$^4$, independently of one another, are each H, C$_{1-12}$-alkyl, C$_{2-12}$-alkenyl or together C$_{2-6}$-alkylene;
R$^5$ is OR$^6$, SO$_2$R$^7$ or OSO$_2$R$^7$;
R$^6$ is H, C$_{1-6}$alkyl or C$_{1-6}$-alkanoyl; and
R$^7$ is C$_{1-6}$alkyl or phenyl or benzyl which is unsubstituted or in each case substituted by halogen, C$_{1-6}$-alkyl or C$_{1-6}$-alkoxy.

2. 1-(1-thioxanthonylcarbonyloxy)-2-[4-(2-hydroxy-2methyl)[propanoylphenoxy]ethane,
   1-(1-thioxanthonylcarbonyloxy)-2-[4-(2-hydroxy-2-methyl)[propanoylphenylthio]ethane,
   1-(3-thioxanthonylthio)-2-[4-(2-hydroxy-2-methyl)-propanoylphenoxymethylenecarbonyloxy]ethane, or
   1-(3-thioxanthonylthio)-2-[4-(2-hydroxy-2-methyl)propanoylphenoxymethylenecarbonylamido]ethane, each being a compound of claim 1.

3. A compound according to claim 1, wherein R$^2$ is bonded to the thioxanthone unit in the 1- or 3-position.

4. A compound according to claim 1, wherein R$^3$ and R$^4$ are each methyl.

5. A compound according to claim 1, wherein R$^5$ is hydroxy.

6. A compound according to claim 1, wherein R$_2$ is carbonyloxyethyleneoxy, carbonyloxyethylenethio, oxymethylenecarbonyloxyethylenethio, or oxymethylenecarbonylamidoethylenethio.

* * * * *